(12) United States Patent
Clouser (10) Patent No.: US 11,505,376 B2
(45) Date of Patent: Nov. 22, 2022

(54) TAMPER-EVIDENT DEVICE

(71) Applicant: Gary L. Sharpe, Naples, FL (US)

(72) Inventor: Doug Clouser, Lewis Center, OH (US)

(73) Assignee: Gary L. Sharpe, Naples, FL (US)

(*) Notice: Subject to any disclaimer, the term of this patent is extended or adjusted under 35 U.S.C. 154(b) by 369 days.

(21) Appl. No.: 16/751,420

(22) Filed: Jan. 24, 2020

(65) Prior Publication Data

US 2020/0262626 A1    Aug. 20, 2020

Related U.S. Application Data

(60) Provisional application No. 62/796,312, filed on Jan. 24, 2019.

(51) Int. Cl.
*B65D 55/02* (2006.01)
*B65D 43/16* (2006.01)

(52) U.S. Cl.
CPC ......... *B65D 55/024* (2013.01); *B65D 43/169* (2013.01)

(58) Field of Classification Search
CPC .... B65D 55/024; B65D 43/169; B65D 39/16; B65D 39/0082; B65D 39/0076; B65D 2401/15; B65D 2401/20; B65D 79/02; B65D 2203/12; B65D 43/18; B65D 43/20; B65D 43/163; B65D 43/164; B65D 55/02; B65D 39/02; B65D 39/04; B65D 47/0823
See application file for complete search history.

(56) References Cited

U.S. PATENT DOCUMENTS

| 2,395,149 | A | * | 2/1946 | Shaw | B65D 51/20 215/249 |
| 3,556,331 | A | * | 1/1971 | Towns | B65D 55/02 215/216 |
| 4,231,486 | A | * | 11/1980 | Bock | B65D 21/022 215/250 |
| 4,482,071 | A | * | 11/1984 | Ishiwatari | B65D 55/08 215/251 |
| 4,619,651 | A | * | 10/1986 | Kopfer | A61J 1/2096 604/87 |
| 4,711,372 | A | * | 12/1987 | Gach | B65D 47/0885 222/23 |
| 4,902,270 | A | * | 2/1990 | Comeau | B01L 3/50825 422/916 |

(Continued)

FOREIGN PATENT DOCUMENTS

| CA | 2763198 A1 | * | 6/2013 | ............... B65B 7/16 |
| FR | 2547897 A1 | * | 12/1984 | ............. B65D 55/02 |

(Continued)

*Primary Examiner* — J. Gregory Pickett
*Assistant Examiner* — Abigail Elizabeth Guidry
(74) *Attorney, Agent, or Firm* — Standley Law Group LLP; Jeffrey Standley; Jeffrey Norris (57) ABSTRACT

A device adapted to provide evidence of tampering. The device comprises a sleeve and an insert that is positioned within the sleeve. The insert comprises a flap that is movable between a closed position and an open position. In particular, the flap is adapted to move from a closed position to an open position when the position of the sleeve relative to the insert is changed a predetermined amount to try to open the container. As a result, an open position of the flap would readily indicate tampering to a user. A system comprising a tray adapted to receive at least one said device is also provided.

17 Claims, 8 Drawing Sheets

(56) References Cited

U.S. PATENT DOCUMENTS

| | | | | |
|---|---|---|---|---|
| 6,050,435 | A * | 4/2000 | Bush | B65D 47/2031 222/541.9 |
| 6,536,618 | B1 * | 3/2003 | Hwang | B65D 39/12 215/361 |
| 6,769,560 | B1 * | 8/2004 | Lin | B65D 39/12 215/361 |
| 7,032,631 | B2 * | 4/2006 | Py | A61L 2/08 141/285 |
| 7,222,736 | B1 * | 5/2007 | Seijas | A61J 7/04 116/318 |
| 7,243,689 | B2 * | 7/2007 | Py | B29C 65/1654 141/2 |
| 7,850,030 | B2 * | 12/2010 | Lin | B65D 39/12 215/361 |
| 8,056,745 | B2 * | 11/2011 | Yu | A47J 41/0027 220/254.3 |
| 8,272,526 | B1 * | 9/2012 | Vovan | B65D 43/0254 215/253 |
| 8,381,905 | B1 * | 2/2013 | Kao | B25H 3/003 206/378 |
| 8,485,359 | B2 * | 7/2013 | Anderson | B65D 51/2807 206/459.1 |
| 8,639,155 | B2 * | 1/2014 | Kato | G03G 15/0855 220/254.1 |
| 8,733,562 | B2 * | 5/2014 | Kao | B25H 3/04 211/94.01 |
| 9,078,535 | B1 * | 7/2015 | Buck | A47G 19/2205 |
| 9,402,782 | B2 * | 8/2016 | Browne | A61J 1/00 |
| 9,440,774 | B2 * | 9/2016 | Schick | B65D 55/024 |
| 9,517,922 | B2 * | 12/2016 | Marantis | A61J 1/1418 |
| 10,064,473 | B2 * | 9/2018 | Julien | A45D 40/0075 |
| 10,329,060 | B2 * | 6/2019 | Weisshaupt | A61L 2/26 |
| 10,479,561 | B2 * | 11/2019 | Nakatani | B65D 51/002 |
| 11,230,421 | B2 * | 1/2022 | Marantis | A61M 1/0011 |
| 2003/0098252 | A1 * | 5/2003 | Sykes | E05B 73/0023 |
| 2003/0141273 | A1 * | 7/2003 | Osti | B65D 23/00 206/581 |
| 2007/0062962 | A1 * | 3/2007 | Iwahara | B62D 25/24 439/798 |
| 2009/0152232 | A1 * | 6/2009 | Chen | B65D 39/04 215/308 |
| 2011/0147335 | A1 * | 6/2011 | Garcia | B65D 39/00 215/230 |
| 2012/0312770 | A1 * | 12/2012 | Agarkov | B65D 39/12 215/253 |
| 2014/0312047 | A1 * | 10/2014 | Yon | B65D 39/04 215/355 |
| 2014/0353274 | A1 * | 12/2014 | Benson | B65D 50/045 215/44 |
| 2015/0217912 | A1 * | 8/2015 | Luzaich | B65D 51/244 220/254.1 |
| 2015/0266632 | A1 * | 9/2015 | Kieffer | B65D 47/0838 220/268 |
| 2016/0058226 | A1 * | 3/2016 | Christopoulos | B65D 51/28 220/254.1 |
| 2016/0185489 | A1 * | 6/2016 | Garcia | B65D 47/12 215/227 |
| 2019/0168918 | A1 * | 6/2019 | Georgelos | F16K 15/16 |
| 2020/0087036 | A1 * | 3/2020 | Azar | C12L 9/00 |

FOREIGN PATENT DOCUMENTS

| | | | |
|---|---|---|---|
| FR | 2715381 A1 | 7/1995 | |
| FR | 2924099 A1 * | 5/2009 | B65D 51/2864 |
| KR | 20-0417222 Y1 | 5/2006 | |
| KR | 20-2012-0004514 U | 6/2012 | |
| WO | WO-2005051775 A2 * | 6/2005 | B65D 51/1672 |
| WO | WO-2011022796 A2 * | 3/2011 | B65D 47/0804 |
| WO | WO-2016088034 A1 * | 6/2016 | B65D 1/023 |
| WO | WO-2021054825 A1 * | 3/2021 | B65D 39/0076 |

* cited by examiner

TAMPER-EVIDENT DEVICE

This application claims the priority benefit of U.S. Provisional Application No. 62/796,312, filed Jan. 24, 2019, which is hereby incorporated by reference in its entirety.

BACKGROUND AND SUMMARY OF THE INVENTION

Exemplary embodiments of the present invention relate generally to a device that is designed to provide evidence of tampering.

Various types of containers require evidence of tampering. Evidence of tampering is particularly important with respect to ingestible or absorbable items (e.g., medicines, foods, etc.). Nevertheless, evidence of tampering may also be important for other reasons. For instance, evidence of tampering may also help to ensure delivery and receipt of an undamaged product.

One known type of evidence of tampering is a cover layer comprised of aluminum foil, plastic, fibrous material, and/or other material that is bonded to a rim of container. Even for a legitimate user, it can often be difficult to access the cover layer to try to peel it from the rim of the container. Once accessed, it may still require a significant amount of effort or force to adequately remove the cover layer in order to access the contents of the container.

Some other types of evidence of tampering may require an even greater amount of effort or force in order to open a container. Others may be more complex or costly to manufacture. Many suffer from a combination of the aforementioned or other drawbacks.

In light of the shortcomings of the known art, there is a need for a tamper-evident device that is relatively easy to access. There is a further need for a tamper-evident device that is easy to manipulate to legitimately access the contents of a container. Needs also exist for a tamper-evident device that is relatively simple to operate and/or less costly to manufacture. In light of the aforementioned needs, there is also a need for a device that provides clear evidence of tampering.

Exemplary embodiments of the claimed invention may satisfy any or all of the aforementioned needs. An exemplary device of the claimed invention is adapted to fit over an opening of a container. In an exemplary embodiment, the device comprises a sleeve and an insert that is positioned within the sleeve, wherein the insert comprises a flap that is movable between a closed position and an open position. In particular, the flap is adapted to move from a closed position to an open position when the position of the sleeve relative to the insert is changed a predetermined amount to try to open the container. As a result, an open position of the flap may readily indicate tampering to a user.

Another exemplary embodiment may comprise a system that comprises a tray adapted to be used in association with at least one of the aforementioned exemplary devices. In one exemplary embodiment, a tray may be used to organize and/or facilitate the transfer of at least one of the aforementioned exemplary devices, more preferably a plurality of the aforementioned exemplary devices. In one further example, a plurality of the trays may be adapted to be stacked or nested to facilitate the organization and/or transfer of an even greater number of the aforementioned exemplary devices.

Exemplary embodiments of a device and/or system may be useful anywhere and for any contents where there is a need for evidence of tampering. Such uses may include, but are not limited to, use in medical facilities (e.g., hospitals, clinics, doctor offices, etc.) or for personal use. Various possibilities exist. Unless otherwise expressly set forth, it is not intended to limit the contents (e.g., food, medicines, perishable items, etc.) or the location or type of use of exemplary embodiments of a device and/or system of the present invention.

In addition to the novel features and advantages mentioned above, other benefits will be readily apparent from the following descriptions of the drawings and exemplary embodiments.

BRIEF DESCRIPTION OF THE DRAWINGS

FIG. 2 is a top plan view of the device of FIG. 1, which indicates a cross-section line A-A.

FIG. 3 is a cross-sectional view of the device of FIG. 2 along line A-A, wherein a Detail B is indicated. Dimensions and descriptions for one example are also provided.

FIG. 4 shows Detail B of FIG. 3. An additional dimension for one example is also provided.

DETAILED DESCRIPTION OF EXEMPLARY EMBODIMENT(S)

Exemplary embodiments of the present invention are directed to a device adapted to provide evidence of tampering. Exemplary embodiments are also directed to a system comprising a tray adapted to receive at least one of such devices.

FIGS. 1-4 show an exemplary embodiment of a device 10 that is adapted to provide evidence of tampering. Device 10 is comprised of a sleeve 20 and an insert 40, which is positioned within the sleeve 20. In operation, the device 10 is adapted to be positioned over an opening of a container (e.g., as a cap for a container).

In this exemplary embodiment, sleeve 20 is substantially cylindrical, which may be particularly beneficial for facilitating use of the device 10 with a variety of types of container openings. In other embodiments, however, a sleeve may have any other suitable shape that will allow the device to be used with a desired container opening.

Figure 1:
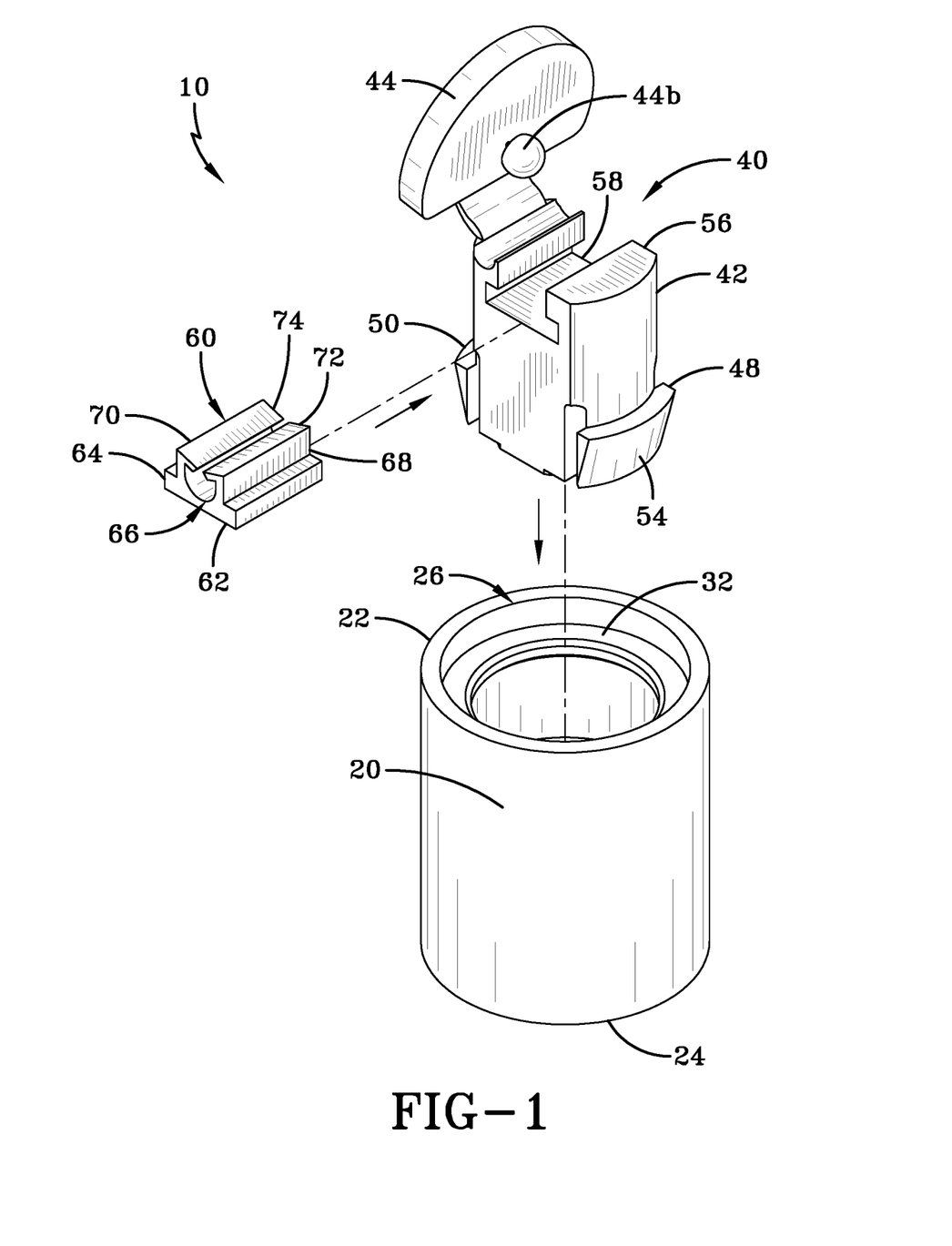
FIG. 1 is a perspective and exploded view of an exemplary embodiment of a device of the present invention.

In this embodiment, sleeve 20 has a first end 22 and a second end 24. Such as indicated in FIG. 1, first end 22 defines a first opening 26 that is configured to receive insert 40. On the other hand, second end 24 may comprise a wall 28 that extends inwardly from the outside of the sleeve 20 to define a second opening 30. Opening 30 is configured to allow device 10 to be positioned over an opening of a container. In this exemplary embodiment, each of first opening 26 and second opening 30 have a circular cross-section. However, in other exemplary embodiments, a first opening and a second opening may have any suitable shapes that facilitate their respective uses.

Figures 2, 3, 4:
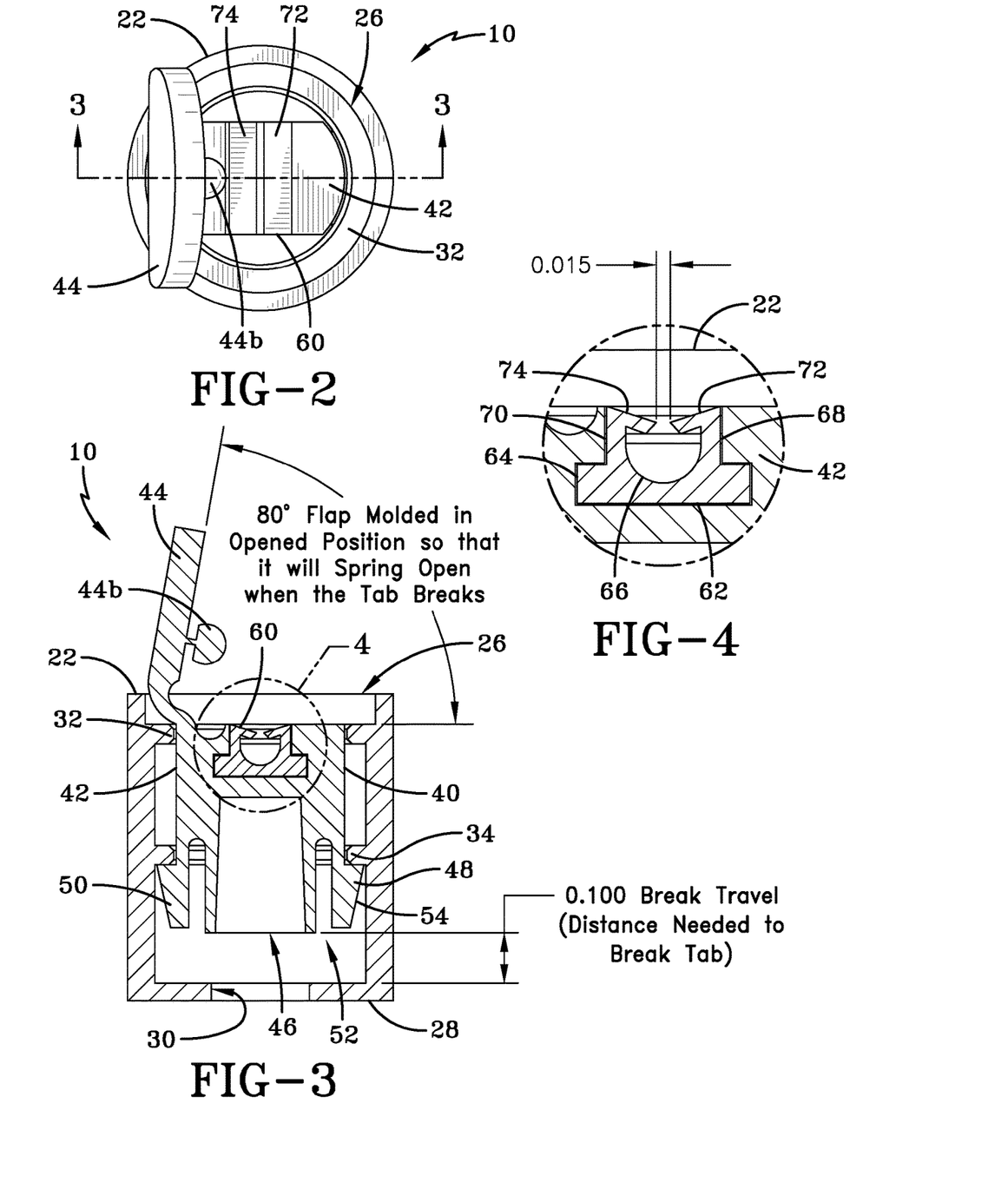

An interior of sleeve 20 further defines at least one ledge that is adapted to engage insert 40. In particular, in this exemplary embodiment, sleeve 20 defines a first ledge 32 and a second ledge 34. Other embodiments may have only one or additional ledges. For instance, in another embodiment, ledge 32 and ledge 34 may be combined into a single ledge. Back to this example, each ledge 32, 34 extends completely around the interior of the sleeve 20. However, in other embodiments, either ledge may extend only partially around the interior of the sleeve. In this example, ledge 32 is adapted to assist with engaging insert 40. In operation, as will be further explained later, ledge 32 is also adapted to assist with activating the evidence of tampering. On the other hand, ledge 34 is also adapted to assist with engaging insert 40. Ledge 34, as will be further explained later, is also adapted to retain insert 40 within sleeve 20, while also allowing a predetermined amount of movement of sleeve 20 relative to insert 40 in order to allow for activation of the evidence of tampering.

Insert 40 is comprised of a body 42 and a flap 44 (i.e., tip cap). Body 42 may have any suitable shape that facilitates positioning of the insert 40 within sleeve 20. As will be further explained, flap 44 facilitates evidence of tampering.

Body 42 defines an opening 46. In operation, opening 46 is adapted to be positioned over an opening of a container. In this exemplary embodiment, opening 46 is adapted to frictionally engage the container around its opening to resist movement of the insert 40 relative to the container during operation of the device 10. After operation of the device 10 in this exemplary embodiment, sufficient force may be applied to remove device 10 from the container. In other exemplary embodiments, an opening defined by the body of the insert may have any suitable configuration to engage a container around its opening. For instance, one example of an opening defined by a body may allow for the insert to be screwed onto a container around its opening.

Body 42 further defines at least one flange or prong that is adapted to facilitate positioning and retention of insert 40 in sleeve 20. In this exemplary embodiment, body 42 defines a flange or prong 48 and a flange or prong 50. Such as can be seen in the example of FIG. 3, flange or prong 48 and flange or prong 50 are adapted to engage (e.g., snap or flex over) ledge 34 to prevent or at least resist against insert 40 backing out of opening 26 of sleeve 20. In this embodiment, such as identified with respect to flange or prong 48, there is a space 52 provided between flange or prong 48 and the portion of the body 42 that forms the opening 46. In this example, space 52 may allow flange or prong 48 to flex inwardly to facilitate positioning of insert 40 in sleeve 20. Moreover, in this embodiment, flange or prong 48 has a beveled surface 54 that also facilitates positioning of insert 40 in sleeve 20. More particularly, in this embodiment, beveled surface 54 facilitates positioning (e.g., sliding) of the insert 40 over ledge 32 and ledge 34 when inserting insert 40 in sleeve 20, and a proximal portion of beveled surface 54 protrudes outward to subsequently resist against insert 40 backing out of opening 26 of sleeve 20 by catching against ledge 34 (and thereafter, ledge 32, if necessary). There is also a similar space and beveled surface with respect to flange or prong 50 in this embodiment. Other embodiments may have other configurations or material compositions that facilitate positioning and retention of an insert in a sleeve to allow for operation as disclosed herein.

In this exemplary embodiment, an upper surface 56 of body 42 defines a track 58, which is adapted to receive a trap 60. In particular, trap 60 is adapted to be slid into track 58 prior to operation of device 10. In such an embodiment, trap 60 may be considered to be a portion of body 42, or it may be considered to be a separate device from body 42. In other embodiments, a trap may be an integral or fixed portion of a body of an insert.

In this exemplary embodiment, trap 60 comprises at least one flange that retains trap 60 in track 58 during operation of device 10. In particular, trap 60 comprises a flange 62 and a flange 64 in this embodiment, which are interconnected to form a base. Trap 60 also comprises an opening 66, wherein at least one flange or prong facilitates reception and retention of a portion of flap 44 in opening 66, as will be later explained in more detail. In this exemplary embodiment, trap 60 comprises a first flange or prong 68 and a second flange or prong 70 that are connected at the base to form opening 66, wherein flanges 62, 64 respectively extend outwardly from flanges or prongs 68, 70. Additionally, in this embodiment, flange or prong 68 comprises a beveled surface 72 that extends downwardly from a top portion of flange or prong 68, and flange or prong 70 comprises a beveled surface 74 that extends downwardly from a top portion of flange or prong 70. In this example, beveled surfaces 72, 74 cooperate to facilitate reception and retention of a portion of flap 44 in opening 66 during operation of device 10. More particularly, in this embodiment, beveled surfaces 72, 74 cooperate to allow a portion of flap 44 to slide into opening 66, wherein the downward angles of beveled surfaces 72, 74 subsequently facilitate resistance against that portion of flap 44 backing out of opening 66. Other exemplary embodiments may comprise other suitable configurations to facilitate reception and retention of a portion of a flap during operation of the device as disclosed herein.

In this exemplary embodiment, flap 44 is rotatably connected to body 42. Such as shown in the example of FIGS. 1 and 3, flap 44 may be initially and flexibly molded in an 80° open position, such that flap 44 is biased in an open position. As will be further explained later, the biased open position is adapted to facilitate an indication of tampering during operation of device 10. However, other exemplary embodiments may have a flap having any suitable connection to body 42 with more or less bias (e.g., no bias) and still facilitate an indication of tampering.

In this exemplary embodiment, flap 44 comprises a protrusion 44b (e.g., a tab). Protrusion 44b is adapted to be received and retained in opening 66 of trap 60. In this embodiment, protrusion 44b is mushroom-shaped, which is particularly beneficial for facilitating removal of protrusion 44b from flap 44 when device 10 indicates tampering. However, other exemplary embodiments may comprise a flap having a protrusion of a different shape that facilitates reception and retention in a trap.

In particular, during use of device 10, trap 60 is adapted to receive protrusion 44b in opening 66 such that flap 44 is initially in a closed position, which is indicative of an absence of tampering. For example, in order to be inserted in opening 66, protrusion 44b may be pushed between beveled surfaces 72, 74 of flanges or prongs 68, 70, or protrusion 44b may be slid into opening 66 such as during insertion of trap 60 in body 42. In such a closed position of this exemplary embodiment, a distal portion of flap 44 extends over ledge 32 and is surrounded by sleeve 20, which may hinder access to flap 44 to discourage tampering. Also, in this example, when flap 44 is in a closed position, sleeve 20 may freely spin around insert 40, which may help to prevent a false indication of tampering. However, other exemplary embodiments may allow for more access to a flap and/or may only allow for limited or no rotation of a sleeve around an insert.

In this exemplary embodiment, when flap 44 is in a closed position, sleeve 20 may only (other than the aforementioned spinning) be pulled or pushed upward relative to insert 40 (e.g., slid upward relative to insert 40) due to the engagement of flanges or prongs 48, 50 with ledge 34. As a result, when there is tampering (or legitimate opening), a user may pull or push up on sleeve 20 to open the container. Due to the engagement (e.g., frictional engagement) of body 42 around the opening of the container, the body 42 may resist movement when the aforementioned user pulls or pushes up on sleeve 20. In this example, a limited amount of upward movement of sleeve 20 relative to insert 40 is adapted to clause ledge 32 to force flap 44 upward, eventually causing protrusion 44b to be cut or otherwise break away from flap 44. When this occurs, protrusion 44b is retained in opening 66 of trap 60, while the flap 44 moves to an open position (not necessarily all the way back to an originally molded position) due to the open bias of flap 44. Consequently, when a legitimate user sees flap 44 in an open position prior to any attempt to remove device 10 from a container, it is a clear indication to the user that there has been tampering with the container. The absence of protrusion 44b would also be further evidence of tampering.

As indicated in the example of FIG. 3, only 0.1-inch or less of upward movement of sleeve 20 relative to insert 40 is necessary to cut or otherwise break protrusion 44b away from flap 44. Moreover, in this embodiment, only a minimal amount of force by the user is required to cause such movement of sleeve 20. As such, an exemplary embodiment may promptly and efficiently provide evidence of tampering. However, other exemplary embodiments may require a further travel distance or more strenuous force to remove a protrusion from a flap.

Other exemplary embodiments may also utilize other suitable types of movement of a sleeve relative to an insert to facilitate evidence of tampering. For example, if there is a threaded engagement between an insert and a sleeve and/or between an insert and a container opening, then unscrewing of the sleeve and/or the insert may cause evidence of tampering.

An exemplary embodiment of a device 10 according to FIGS. 1-4 is particularly adapted to be used to detect tampering of a syringe. In particular, a tip of a syringe may be inserted through opening 30 of sleeve 20 and into opening 46 of insert 40. However, other exemplary embodiments of a device may be configured to work with other types of containers that form other types of openings. It is therefore not intended to limit the use of a device for any particular type of container, unless otherwise expressly specified.

Figure 5:
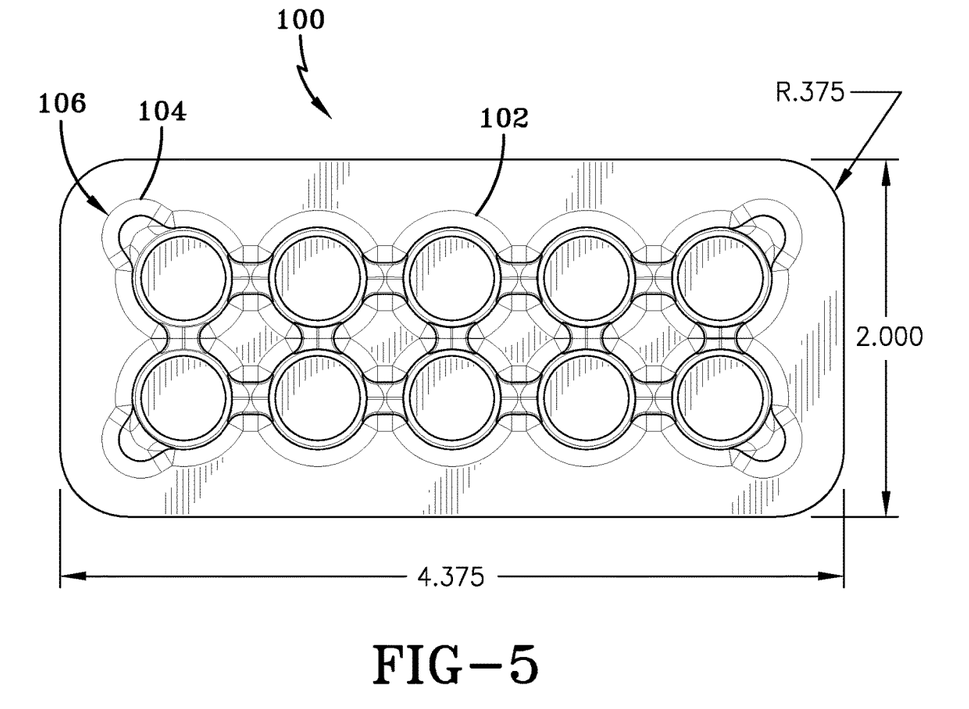
FIG. 5 is a top plan view of an exemplary embodiment of a tray for devices such as shown in FIGS. 1-4. Dimensions for one example are provided.
Figure 6:
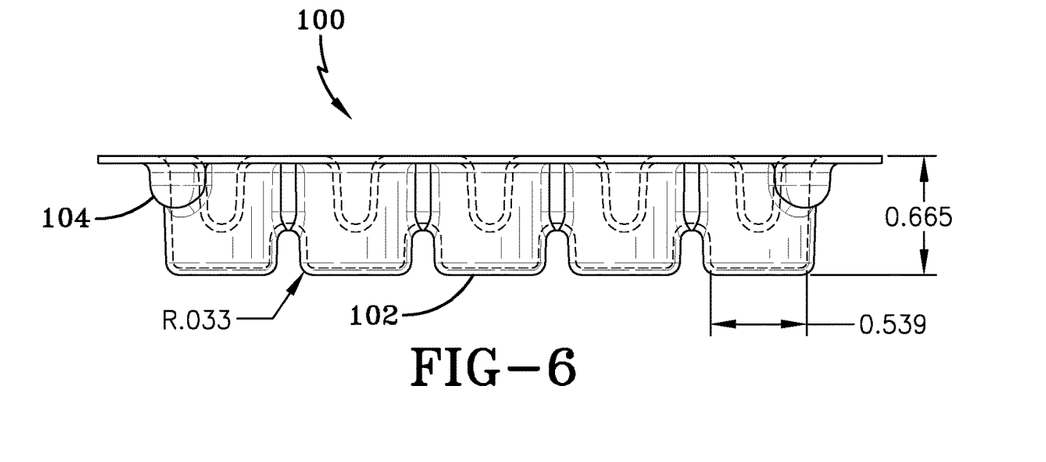
FIG. 6 is a side elevation view of the tray of FIG. 5. Additional dimensions for one example are also provided.
Figure 7:
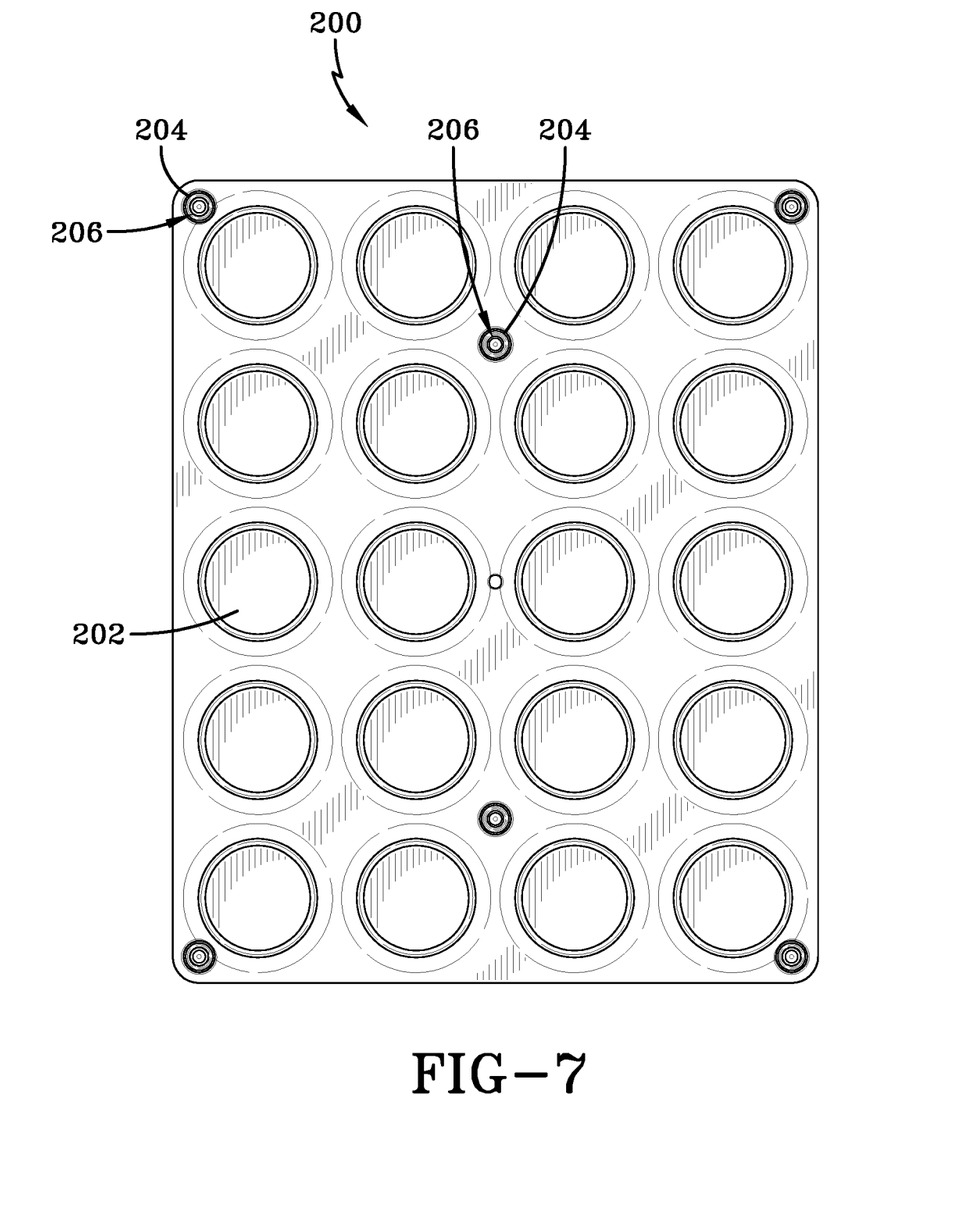
FIG. 7 is a top plan view of a second exemplary embodiment of a tray for devices such as shown in FIGS. 1-4.
Figure 8:
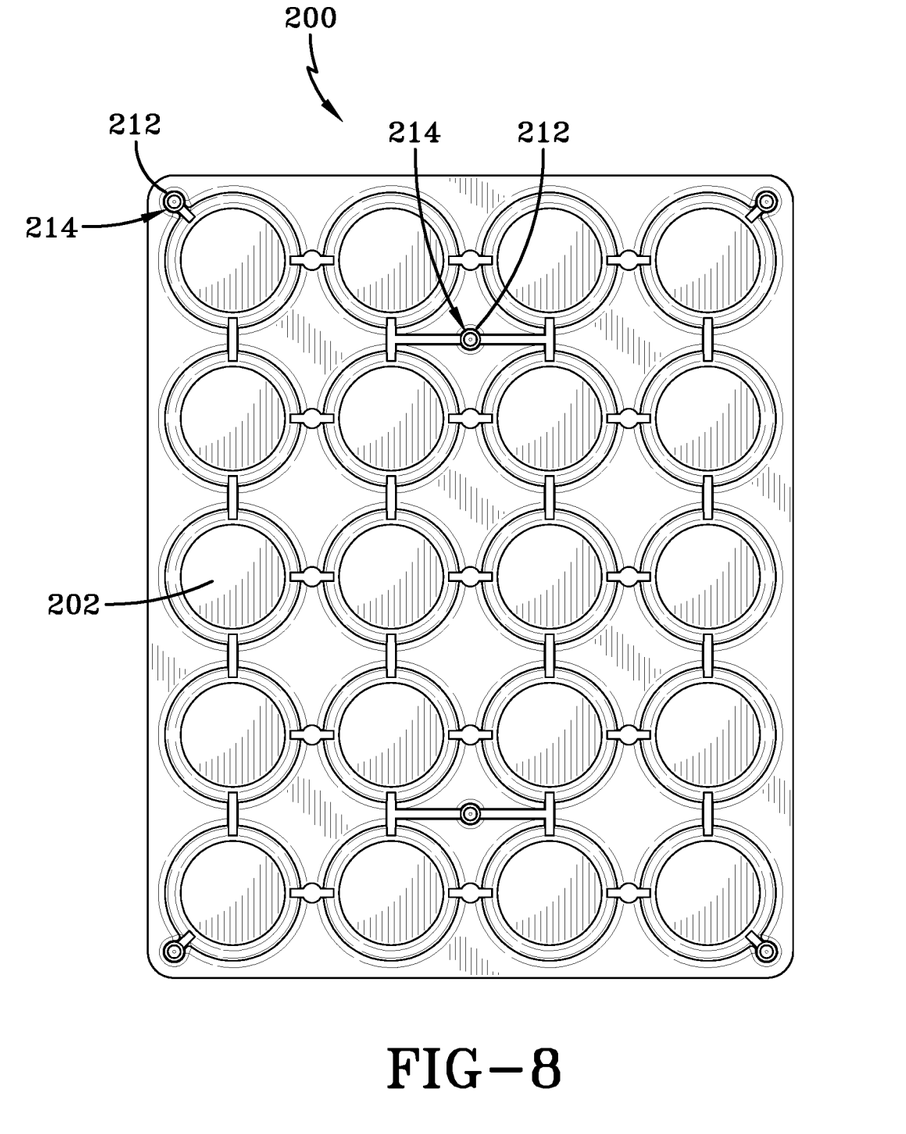
FIG. 8 is a bottom plan view of the tray of FIG. 7.
Figure 9:
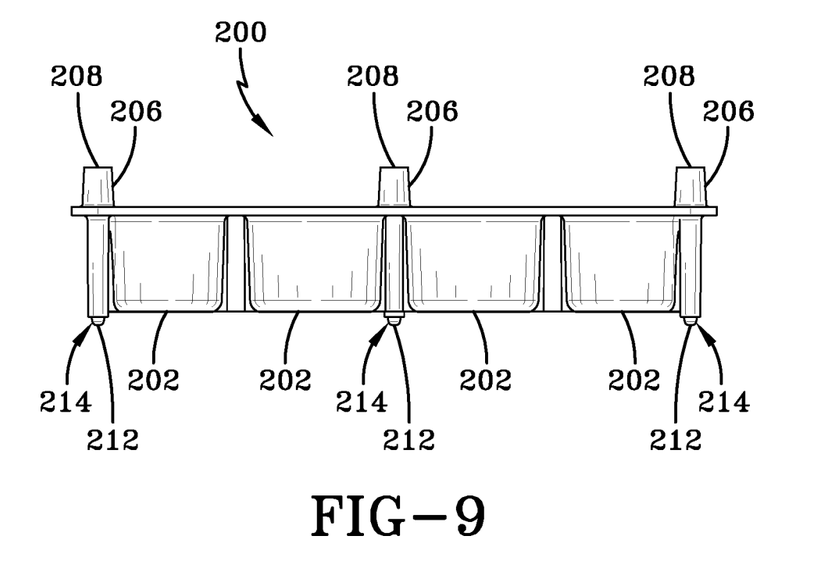
FIG. 9 is a first side elevation view of the tray of FIG. 7.
Figure 10:
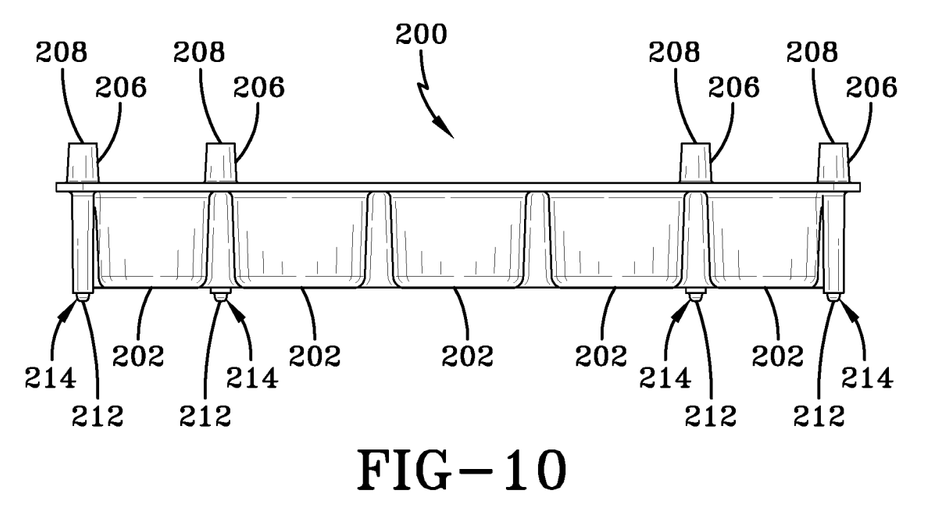
FIG. 10 is a second side elevation view of the tray of FIG. 7.
Figure 11:
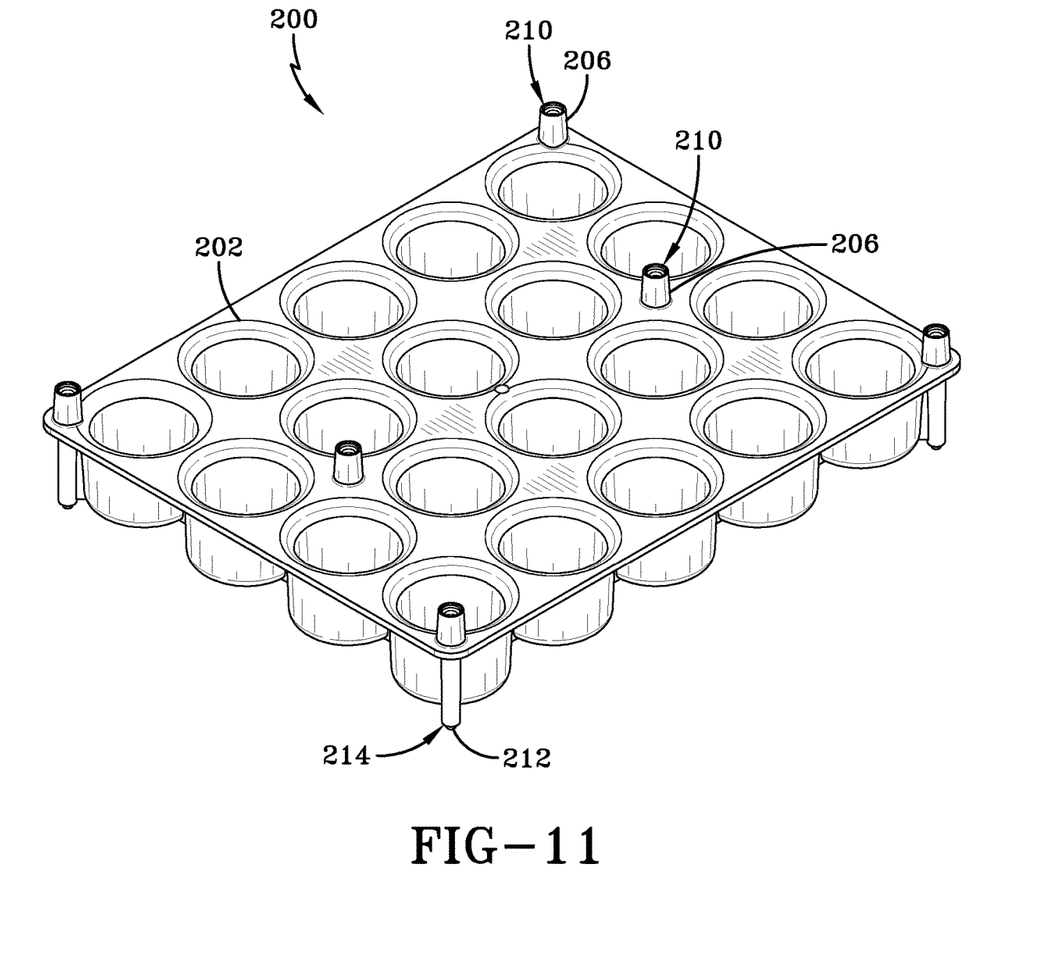
FIG. 11 is a top perspective view of the tray of FIG. 7.
Figure 12:
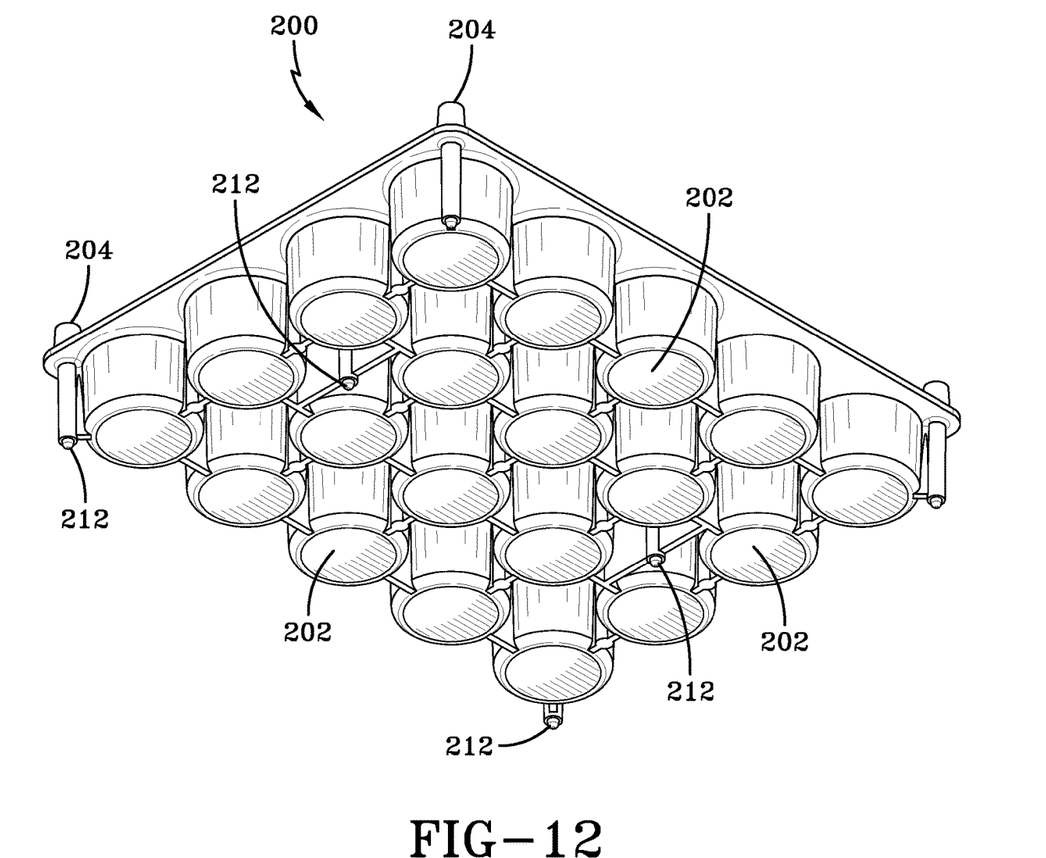
FIG. 12 is a bottom perspective view of the tray of FIG. 7.

FIGS. 5 and 6 show an example of a tray 100 for devices 10. In particular, this embodiment of tray 100 has ten receptacles 102 that are respectively adapted to receive ten of devices 10. Tray 100 also includes at least one nesting feature 104. In this example, there is a nesting feature 104 that forms a recess 106 in a top surface near each corner of tray 100, wherein each nesting feature 104 extends from a respective receptacle 102. A nesting feature 104 may facilitate stacking of multiple trays such as for storage, packaging, and/or shipment of the trays. In this embodiment, a nesting feature 104 may receive a portion of another tray in a recess 106 to facilitate stacking of the trays. Although not shown for ease of illustration, a Teflon™ or other suitable seal may cover tray 100 to secure devices 10 in tray 100 such as for storage or shipment. Other exemplary embodiments of a tray may include a different number or configuration of receptacles, a different stacking configuration, and/or a different type of cover.

Another example of a tray 200 is shown in FIGS. 7-12. As compared to tray 100, tray 200 comprises a different configuration having a different number of receptacles and a different nesting configuration. In this exemplary embodiment, tray 200 has twenty receptacles 202 that are respectively adapted to receive twenty of devices 10. Tray 200 also includes at least one nesting feature 204. In this example, there are six nesting features 204 that each form a projection 206 that extends above a top surface of tray 200 and may serve as a pedestal when stacking trays such as for storage, packaging, and/or shipment of the trays. In particular, there is one nesting feature 204 near each corner of tray 200, and two nesting features 204 that are centrally located for increased stability when stacking multiple larger trays. Furthermore, in this embodiment, a top surface 208 of each nesting feature 204 forms a recess 210 that is adapted to receive a portion of another tray to further facilitate stacking of trays. This exemplary embodiment also comprises six complementary nesting features 212 on a bottom surface of tray 200 to facilitate stacking in conjunction with nesting features 204 of another tray. In particular, each nesting feature 212 comprises a projection 214 that is adapted to be received in a recess 210 of another tray. While the nesting configurations of trays 100 and 200 may be particularly beneficial, other suitable configurations for stacking (e.g., nesting) of trays may be implemented in other exemplary embodiments. Also, similar to tray 100, a Teflon™ or other suitable seal (not shown for ease of illustration) may cover tray 200 to secure devices 10 in tray 200 such as for storage or shipment. Again, other exemplary embodiments of a tray may include a different number or configuration of receptacles, a different stacking configuration, and/or a different type of cover.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain some of the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A device adapted to provide evidence of tampering with a container, said device comprising:
   a sleeve having an interior that defines at least a first ledge; and
   an insert positioned within said sleeve, said insert comprising a flap that is movable between a closed position and an open position;
   wherein said sleeve is adapted to be moved relative to said insert when there is an attempt to open a container, and said flap is adapted to move from said closed position to said open position when a position of said sleeve relative to said insert is changed a predetermined amount such that said first ledge is adapted to engage said flap, wherein said open position of said flap is adapted to indicate tampering.

2. The device of claim 1 wherein:
said sleeve comprises a first end and a second end;
said first end defines a first opening in which said insert is positioned; and
said second end comprises a wall that extends inwardly from an outside of said sleeve to define a second opening, said second opening configured to allow said device to be positioned over an opening of a container.

3. The device of claim 1 wherein said ledge extends completely around said interior of said sleeve.

4. The device of claim 1 further comprising:
a second ledge defined by said interior of said sleeve that is adapted to allow a sufficient amount of movement of said sleeve relative to said insert in order to allow for activation of evidence of tampering;
wherein said second ledge is further adapted to engage said insert to retain said insert in said sleeve during operation of said device.

5. The device of claim 1 wherein:
said insert further comprises a body that defines an opening that is adapted to be positioned over an opening of a container.

6. The device of claim 5 wherein said flap is rotatably connected to said body.

7. The device of claim 5 wherein said body further comprises at least one prong that is adapted to facilitate positioning and retention of said insert in said sleeve.

8. The device of claim 7 wherein said at least one prong is adapted to flex inwardly toward a portion of said body that defines said opening in order to facilitate positioning of said insert in said sleeve.

9. The device of claim 7 wherein said at least one prong has a beveled surface that facilitates positioning and retention of said insert in said sleeve.

10. The device of claim 9 wherein a proximal portion of said beveled surface protrudes outward to facilitate resistance against said insert backing out of said sleeve.

11. The device of claim 5 further comprising a trap associated with said body, said trap adapted to receive and retain a portion said flap to facilitate additional evidence of tampering.

12. The device of claim 11 wherein:
said trap is adapted to receive said portion of said flap when said flap is in a closed position; and
said trap is adapted to retain said portion of said flap when said flap moves to an open position;
wherein retention of said portion of said flap in said trap is additional evidence of tampering.

13. The device of claim 11 wherein said trap is slidably positioned in said body.

14. The device of claim 11 wherein:
an upper surface of said body defines a track; and
said trap comprises at least one flange that retains said trap in said track during operation of said device.

15. The device of claim 11 wherein:
said trap comprises at least one prong that forms an opening;
wherein said at least one prong facilitates reception and retention of said portion of said flap in said opening of said trap.

16. The device of claim 15 wherein:
said at least one prong of said trap comprises a beveled surface that extends downwardly from a top portion of said at least one prong of said trap;
said beveled surface is adapted to allow said portion of said flap to slide into said opening of said trap for said flap to be in said closed position; and
a downward angle of said beveled surface facilitates retention of said portion of said flap in said opening of said trap when said flap is moved to said open position.

17. The device of claim 11 wherein said portion of said flap is a protrusion that is mushroom-shaped.

* * * * *